(12) United States Patent
Liu et al.

(10) Patent No.: US 7,982,059 B2
(45) Date of Patent: Jul. 19, 2011

(54) SORBITOL CONVERSION PROCESS

(75) Inventors: Aiguo Liu, Louisville, KY (US);
Christopher C. Luckett, Louisville, KY (US)

(73) Assignee: Sud-Chemie Inc., Louisville, KY (US)

( * ) Notice: Subject to any disclaimer, the term of this patent is extended or adjusted under 35 U.S.C. 154(b) by 553 days.

(21) Appl. No.: 12/060,929

(22) Filed: Apr. 2, 2008

(65) Prior Publication Data

US 2008/0249323 A1 Oct. 9, 2008

Related U.S. Application Data

(60) Provisional application No. 60/910,595, filed on Apr. 6, 2007.

(51) Int. Cl.
*C07D 493/06* (2006.01)
(52) U.S. Cl. ....................................................... 549/464
(58) Field of Classification Search .................... 549/464
See application file for complete search history.

(56) References Cited

U.S. PATENT DOCUMENTS

| | | | |
|---|---|---|---|
| 1,757,468 A | 5/1930 | Muller | |
| 2,572,566 A | 10/1951 | Himel | |
| 2,899,470 A | 8/1959 | Goldstein et al. | |
| 3,160,641 A | 12/1964 | Hartmann | |
| 3,558,725 A | 1/1971 | Kohno | |
| 3,579,380 A | 5/1971 | Friese | |
| 4,008,285 A | 2/1977 | Melaja | |
| 4,313,884 A | 2/1982 | Arena | |
| 4,401,823 A | 8/1983 | Arena | |
| 4,431,830 A | 2/1984 | Schonafinger | |
| 4,456,774 A | 6/1984 | Sherman et al. | |
| 4,544,778 A | 10/1985 | Chao | |
| 4,861,513 A | 8/1989 | Lueders et al. | |
| 5,998,607 A | 12/1999 | Heikkila | |
| 6,013,812 A | 1/2000 | Haas | |
| 6,271,007 B1 | 8/2001 | Apajalahti | |
| 6,407,266 B2 | 6/2002 | Bhatia | |
| 6,639,067 B1 | 10/2003 | Brinegar et al. | |
| 6,670,033 B1 | 12/2003 | Hubbard et al. | |
| 6,689,892 B2 | 2/2004 | Andrews | |
| 6,699,457 B2 | 3/2004 | Cortright et al. | |
| 6,818,781 B2 | 11/2004 | Bhatia | |
| 6,831,181 B2 | 12/2004 | Bhatia | |
| 6,849,748 B2 | 2/2005 | Moore | |
| 6,864,378 B2 | 3/2005 | Bhatia | |
| 6,894,199 B2 | 5/2005 | Heikkila | |
| 6,911,565 B2 | 6/2005 | Heikkilä et al. | |
| 6,953,873 B2 | 10/2005 | Cortright et al. | |
| 6,964,757 B2 | 11/2005 | Cortright et al. | |
| 6,964,758 B2 | 11/2005 | Cortright et al. | |

OTHER PUBLICATIONS

International Search Report for PCT/US2008/059185 mailed Jul. 7, 2008.

*Primary Examiner* — Taofiq A Solola

(57) ABSTRACT

A process for converting aqueous sorbitol to xylitol and isosorbide in the presence of an acid catalyst, and in the absence of an enzyme or of a hydrogenating catalyst, is disclosed. In the process, a sorbitol solution is reacted with an acid zeolite to produce xylitol and isosorbide.

19 Claims, 2 Drawing Sheets

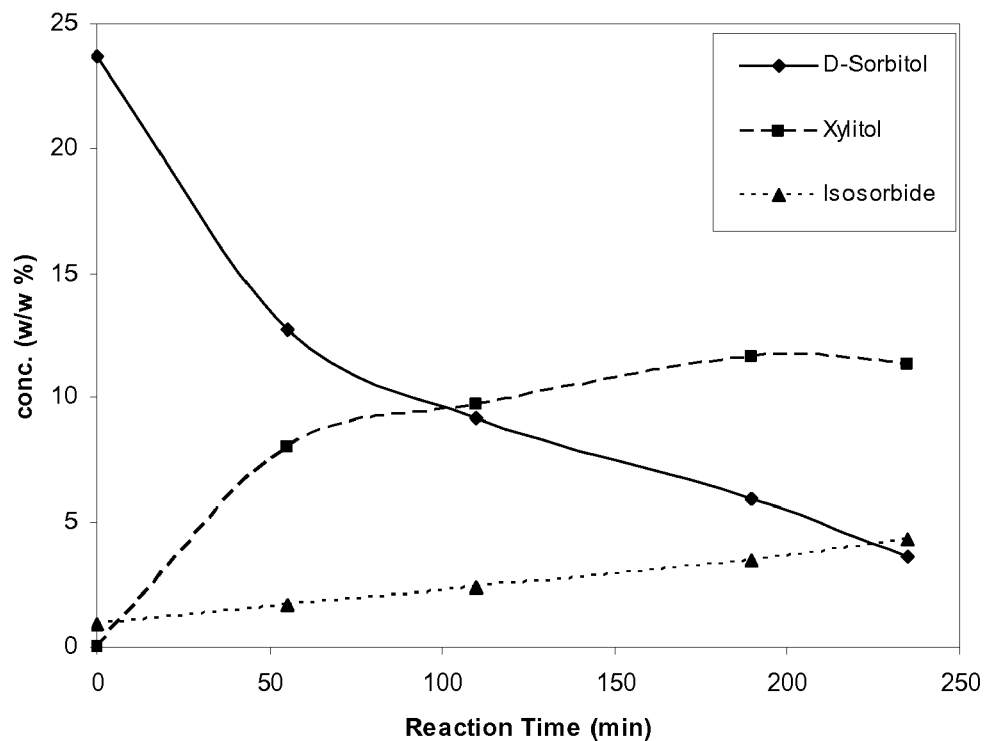
Figure 1 – Sorbitol with Mordenite Zeolite
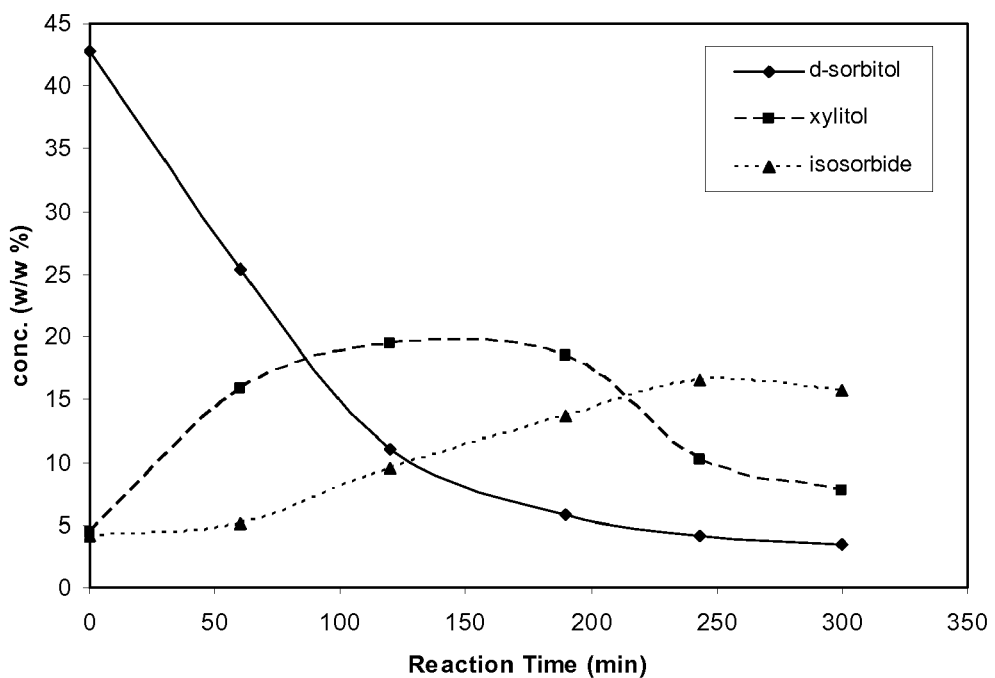
Figure 2 – Sorbitol with 1.5 mm Extrudate Pentasil Zeolite

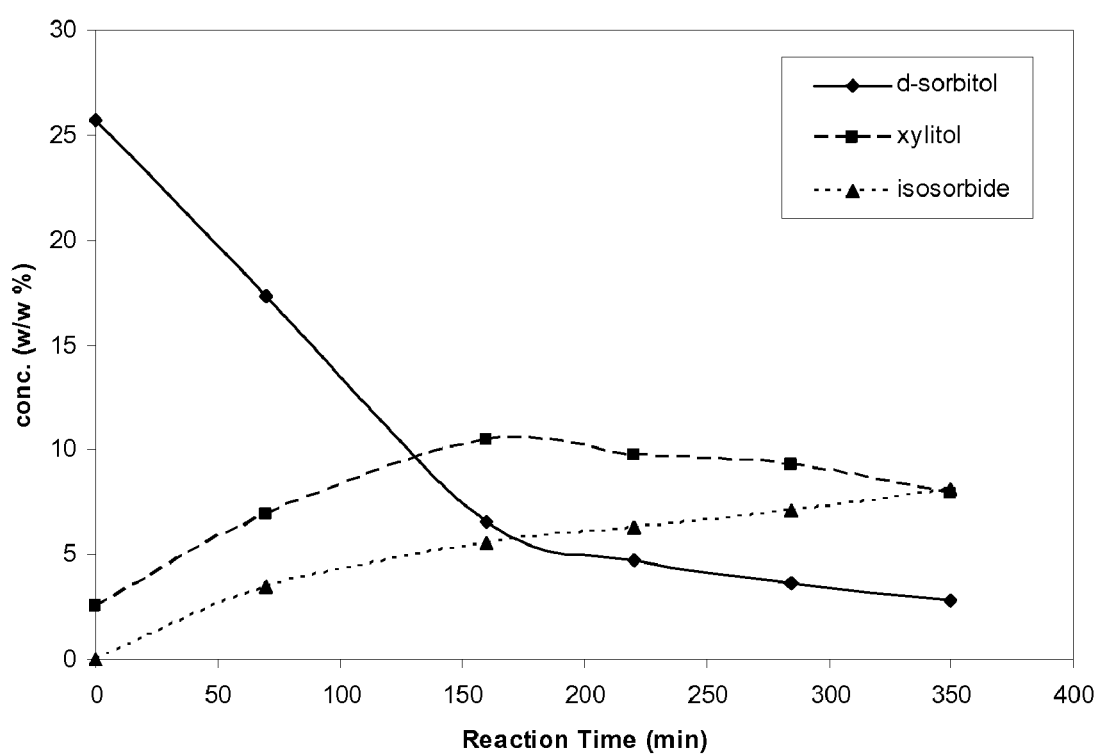
Figure 3 – Sorbitol with 2.5 mm Extrudate Pentasil Zeolite

US 7,982,059 B2

SORBITOL CONVERSION PROCESS

CROSS-REFERENCE TO PRIOR APPLICATIONS

The present application claims priority to U.S. provisional patent application 60/910,595 filed Apr. 6, 2007, incorporated herein by reference.

BACKGROUND

1. The Present Development

The present development is a process for converting aqueous sorbitol to xylitol and isosorbide in the presence of an acid catalyst. Specifically, the process involves reacting an aqueous sorbitol solution with an acid zeolite at a temperature of about 250° C. in a reactor maintained at from about 68 bar to about 80 bar pressure to produce xylitol and isosorbide in high yields.

2. The Prior Art

Xylitol is well known for its extensive uses in the food industry. For example, xylitol is commonly found in diet drinks, chewing gums, ice cream, baked goods and fruit spreads. The global market for xylitol, based on data in 2000, was estimated at €0.97 billion, with sales volumes of 1,397,000 metric tons.

Isosorbide, or 1,4-3,6-dianhydro-D-sorbitol, is known for its therapeutic uses, particularly in the form of mono- or di-nitrate compounds. Isosorbide has also been shown to have utility as a monomer in the manufacture of polymers and copolymers, especially polyester polymers and copolymers. Polymers made of isosorbide tend to exhibit high clarity and mechanical strength.

A common method for production of xylitol is through a multi-step process involving hydrolysis of a xylan-containing material to produce xylose, then conversion of the xylose to xylitol, generally in the presence of a nickel catalyst, such as Raney nickel. Though this method results in the desired conversion, the method tends to be expensive and inefficient because the resulting xylitol must be separated from numerous by-products of the reaction. Alternatively, xylitol may be produced by enzymatic conversion of sugars. However, these methods have not been demonstrated to be effective on a commercial scale.

A common method for production of isosorbide is to contact sorbitol with an acidic catalyst, such as a sulfuric acid catalyst or an acid zeolite, followed by separation and purification. This method results in the desired conversion, but tends to be expensive and difficult to maintain on a commercial scale because of the need for maintaining high vacuum during the reaction. Alternatively, isosorbide may be produced by reacting an aqueous solution of sorbitol with an acid catalyst, including acidic zeolites, and an acid-stable hydrogenating catalyst, at a temperature of greater than 100° C. in a hydrogen atmosphere. However, this method tends to produce a mixture of products that require further separation and purification.

SUMMARY OF THE PRESENT INVENTION

The present development is a process for converting aqueous sorbitol to xylitol and isosorbide in the presence of an acid catalyst, and in the absence of an enzyme or of a hydrogenating catalyst. In the process, an aqueous sorbitol solution is reacted with an acid zeolite at a temperature of about 250° C. in a reactor maintained at from about 68 bar to about 80 bar pressure. The final products are xylitol and isosorbide.

BRIEF DESCRIPTION OF THE FIGURES

FIG. 1 is a graphical depiction using data from a high pressure liquid chromatograph showing the relative concentrations of sorbitol, isosorbide, and xylitol over time as sorbitol is reacted with a mordenite zeolite;

FIG. 2 is a graphical depiction using data from a high pressure liquid chromatograph showing the relative concentrations of sorbitol, isosorbide, and xylitol over time as sorbitol is reacted with an 1.5 mm extruded pentasil zeolite; and FIG. 3 is a graphical depiction using data from a high pressure liquid chromatograph showing the relative concentrations of sorbitol, isosorbide, and xylitol over time as sorbitol is reacted with a 2.5 mm extruded pentasil zeolite.

DETAILED DESCRIPTION OF THE INVENTION

The present development is a process for converting sorbitol to xylitol and isosorbide. The process reacts an aqueous sorbitol solution with an acid catalyst, in the absence of a noble metal or of an enzyme or of a hydrogenating catalyst, at a temperature of at least about 200° C. and at a pressure of from 65 bar to 85 bar.

The sorbitol solution preferably comprises about 25 wt % sorbitol in water. It is anticipated, however, that the sorbitol concentration may range from about 10 wt % to about 80 wt %.

The acid catalyst of the process is preferably an acid zeolite. Examples of acid zeolites that may be used in the process include, but are not limited to, mordenite zeolites, pentasil zeolites, zeolites having an orthorhombic crystal structure with straight 12-membered ring channels and crossed 8-membered ring channels, zeolites having an orthorhombic crystal structure with straight 10-membered ring channels connected by sinusoidal channels. The acid zeolite should not comprise any noble metals, e.g. metals found in Groups VIIB, VIII, and IB of the Periodic Table of Elements.

The sorbitol solution is reacted with the acid zeolite, with agitation, at an elevated temperature under pressure. In a first embodiment, the sorbitol solution and acid catalyst may be combined in a reactor at a temperature of from about 15° C. to about 40° C. The reactor is sealed to allow the reaction to be conducted under pressure. The pressure in the reactor is adjusted to between 65 bar and 85 bar using a hydrogen-free pressure source. Because of its economic benefits, the hydrogen-free pressure source recommended is nitrogen gas, but other gases known in the art to be generally inert to chemical reaction may be used, such as, without limitation, argon gas or helium gas. After the pressure and agitation rate are adjusted, the reaction solution temperature is raised to a predetermined temperature of at least about 200° C. and held within 10° C. of the predetermined temperature until the reaction is complete. In an alternative embodiment, the sorbitol solution is heated to a temperature of at least about 200° C. and added to the acid catalyst in the reactor, the reactor is sealed and the pressure is adjusted to between 65 bar and 85 bar while maintaining the solution temperature and maintaining agitation. In a preferred embodiment, the pressure is held between 68 bar and 80 bar and the reaction temperature is held at about 250° C. during the course of the reaction.

The sorbitol solution is reacted with the acid catalyst for a predetermined time period, preferably ranging from about 60 minutes to about 360 minutes. Progress to reaction completion can be monitored by withdrawing liquid samples and analyzing the samples by techniques known in the art, such as high pressure liquid chromatography (HPLC).

The following are representative examples of the process of the present development. These examples are presented to further explain the invention and are not intended, or to be taken, to limit the scope of the invention.

EXAMPLE 1

About 300 milliliters of an aqueous sorbitol solution, comprising about 25 wt % sorbitol, is added to a mix tank containing about 10 grams pentasil zeolite being in the form of 1.5 mm extrudates. The tank is sealed, the pressure is raised to between 68 bar and 80 bar with nitrogen, and the temperature is controlled to hold at about 250° C. Liquid samples are withdrawn at regular intervals of about 60 minutes for a period of up to 360 minutes, and analyzed by high pressure liquid chromatography (HPLC), after pre-treatment and dilution, to determine the relative concentration of sorbitol remaining and products produced. After about 250 minutes, approximately 92.5% of the sorbitol is converted and the product mixture comprises approximately 47.0% isosorbide and 28.6% xylitol.

EXAMPLE 2

The procedure of Example 1 is followed except a pentasil zeolite being in the form of 2.5 mm extrudates replaces the 1.5 mm extrudate pentasil zeolite. After about 235 minutes, approximately 84.5% of the sorbitol is converted and the product mixture comprises approximately 25.3% isosorbide and 64.7% xylitol.

EXAMPLE 3

The procedure of Example 1 is followed except a mordenite zeolite replaces the 1.5 mm extrudate pentasil zeolite. After about 350 minutes, approximately 84.8% of the sorbitol is converted and the product mixture comprises approximately 39.8% isosorbide and 38.2% xylitol. Gaseous carbon dioxide is also produced in the reaction.

It is understood that one skilled in the art may make alterations to the embodiments shown and described herein without departing from the scope of the invention. For example, it is anticipated that the concentration of sorbitol in the aqueous solution may be increased or decreased without affecting the resultant product mixture.

What is claimed is:

1. A process for converting aqueous sorbitol to xylitol and isosorbide comprising reacting an aqueous sorbitol solution with an acid zeolite in a reactor maintained at from about 65 bar to about 85 bar pressure while maintaining the reaction temperature at least about 200° C., and wherein the process is carried out in the absence of an enzyme or of a hydrogenating catalyst.

2. The process of claim 1 wherein the reaction temperature is maintained at 250° C.±10° C.

3. The process of claim 1 wherein the reactor is maintained at from about 68 bar to about 80 bar pressure.

4. The process of claim 1 wherein the aqueous sorbitol solution comprises from about 10 wt % to about 80 wt % sorbitol in water.

5. The process of claim 4 wherein the aqueous sorbitol solution comprises about 25 wt % sorbitol in water.

6. The process of claim 1 wherein the acid zeolite is selected from the group consisting of mordenite zeolites, pentasil zeolites, zeolites having an orthorhombic crystal structure with straight 12-membered ring channels and crossed 8-membered ring channels, zeolites having an orthorhombic crystal structure with straight 10-membered ring channels connected by sinusoidal channels, and combinations thereof, which are further absent metals found in Groups VIIB, VIII, and IB of the Periodic Table of Elements.

7. A process for converting aqueous sorbitol to xylitol and isosorbide comprising the steps:
    (a) combining an aqueous sorbitol solution having a temperature of from about 15° C. to about 40° C. with an acid zeolite in a reactor with agitation;
    (b) sealing said reactor;
    (c) adding a hydrogen-free pressure source to said reactor, while maintaining agitation, until the pressure in said reactor is between 65 bar and 85 bar;
    (d) heating said reactor until the aqueous sorbitol solution reaches a predetermined temperature of at least about 200° C.;
    (e) maintaining said pressure between 65 bar and 85 bar and said temperature within about a 10° C. range of the predetermined temperature for a predetermined time period; and
    (f) reducing said pressure to about 1 bar and reducing said temperature to from about 15° C. to about 40° C., and isolating xylitol and isosorbide from any residual aqueous sorbitol,
and wherein said process is carried out in the absence of an enzyme or of a hydrogenating catalyst or of a metal found in Groups VIIB, VIII, and IB of the Periodic Table of Elements.

8. The process of claim 7 wherein the reaction temperature is maintained at 250° C.±10° C.

9. The process of claim 7 wherein the aqueous sorbitol solution comprises from about 10 wt % to about 80 wt % sorbitol in water.

10. The process of claim 9 wherein the aqueous sorbitol solution comprises about 25 wt % sorbitol in water.

11. The process of claim 7 wherein the acid zeolite is selected from the group consisting of mordenite zeolites, pentasil zeolites, zeolites having an orthorhombic crystal structure with straight 12-membered ring channels and crossed 8-membered ring channels, zeolites having an orthorhombic crystal structure with straight 10-membered ring channels connected by sinusoidal channels, and combinations thereof, which are further absent metals found in Groups VIIB, VIII, and IB of the Periodic Table of Elements.

12. The process of claim 7 wherein said hydrogen-free pressure source is selected from nitrogen gas, argon gas, helium gas, and combinations thereof.

13. The process of claim 7 wherein step (a) comprises combining an aqueous sorbitol solution heated to a temperature of at least about 200° C. with an acid zeolite in a reactor with agitation.

14. The process of claim 7 wherein said predetermined time period of step (e) ranges from about 60 minutes to about 360 minutes.

15. A process for converting aqueous sorbitol to xylitol and isosorbide consisting essentially of reacting an aqueous sorbitol solution with an acid zeolite for from about 60 minutes to about 360 minutes in a reactor maintained at from about 65 bar to about 85 bar pressure while maintaining the reaction temperature at 250° C.±10° C., wherein said acid zeolite is selected from the group consisting of mordenite zeolites, pentasil zeolites, zeolites having an orthorhombic crystal structure with straight 12-membered ring channels and crossed 8-membered ring channels, zeolites having an orthorhombic crystal structure with straight 10-membered ring channels connected by sinusoidal channels, and combinations thereof.

16. The process of claim 15 wherein said pressure is produced by adding a hydrogen-free pressure source to said reactor.

17. The process of claim 15 wherein said process is carried out in the absence of an enzyme or of a hydrogenating catalyst.

18. The process of claim 15 wherein the aqueous sorbitol solution comprises from about 10 wt % to about 80 wt % sorbitol in water.

19. The process of claim 18 wherein the aqueous sorbitol solution comprises about 25 wt % sorbitol in water.

\* \* \* \* \*